United States Patent [19]

Dorian et al.

[11] Patent Number: 5,521,079
[45] Date of Patent: May 28, 1996

[54] MICROCAPSULE GENERATING SYSTEM CONTAINING AN AIR KNIFE AND METHOD OF ENCAPSULATING

[75] Inventors: Randel E. Dorian, Orinda; Kent C. Cochrum, Davis, both of Calif.

[73] Assignee: The Regents of the University of California, Oakland, Calif.

[21] Appl. No.: 185,709

[22] Filed: Jan. 24, 1994

[51] Int. Cl.$^6$ .................... C12N 11/00; C12N 11/10; C12N 5/00; C12N 1/40
[52] U.S. Cl. .................... 435/174; 264/4.7; 428/402.2; 435/177; 435/178; 435/240.22; 435/284.1; 435/283.1
[58] Field of Search .................... 435/177, 178, 435/179, 180, 182, 288, 240.22; 264/4, 4.7; 428/402.2

[56] References Cited

U.S. PATENT DOCUMENTS

| | | | |
|---|---|---|---|
| 4,352,883 | 10/1982 | Lim | 435/178 |
| 4,386,895 | 6/1983 | Sodickson | 425/5 |
| 4,391,909 | 7/1983 | Lim | 435/178 |
| 4,409,331 | 10/1983 | Franklin | 435/178 |
| 4,663,286 | 5/1987 | Tsang et al. | 435/178 |
| 4,675,140 | 6/1987 | Sparks et al. | 264/4.3 |
| 4,692,284 | 9/1987 | Braden | 264/4.3 |
| 4,789,550 | 12/1988 | Hommel et al. | 424/493 |
| 4,800,160 | 1/1989 | Iguchi et al. | 435/177 |
| 4,814,274 | 3/1989 | Shioya et al. | 435/174 |
| 4,828,997 | 5/1989 | Yamaguchi et al. | 435/178 |
| 4,921,757 | 5/1990 | Wheatley et al. | 428/402.2 |
| 4,956,128 | 9/1990 | Hommel et al. | 264/4 |
| 5,040,960 | 8/1991 | Shioya et al. | 425/5 |

FOREIGN PATENT DOCUMENTS

| | | |
|---|---|---|
| 2034641 | 5/1992 | Canada . |
| 57-136446 | 7/1982 | Japan . |
| 84949 | 4/1957 | Netherlands . |

OTHER PUBLICATIONS

J. Klein, et al., Pore Size and Properties of Spherical Ca–Alginate Biocatalyst, *European Journal of Applied Microbiology and Biotechnology*, 18:86–91 (1983).

A. C. Hulst, et al., A New Technique for the Production of Immobilized Biocatalyst In Large Quantities, *Biotechnology and Bioengineering*, vol. XXVII, pp. 870–876, (1985).

*Primary Examiner*—David M. Naff
*Attorney, Agent, or Firm*—Hana Verny

[57] ABSTRACT

Spherical microcapsules containing biological material such as tissue or living cells are formed with a diameter of less than 300 μm using a microcapsule generating system containing an air knife. The air knife is formed by an air sleeve positioned eccentrically around a needle. An encapsulating material such as an alginate solution containing the biological material to be encapsulated is forced through the needle, while pressurized air is introduced into the air sleeve and flows out an end opening of the sleeve in which the needle is positioned. The pressurized air breaks up the alginate being discharged from the needle. The resultant alginate droplets fall into a collecting tank where they contact a gelling medium, such as $CaCl_2$, so that the outer surface of these droplets harden and microcapsules are formed. In addition to being eccentrically positioned to facilitate very small droplet formation, the needle preferably has a beveled, pointed discharge end surface to enhance droplet size reduction. The beveled end surface of the needle preferably extends beyond the end opening of the sleeve and is positioned facing the center of the air sleeve. The end opening of the air sleeve may also be beveled.

11 Claims, 6 Drawing Sheets

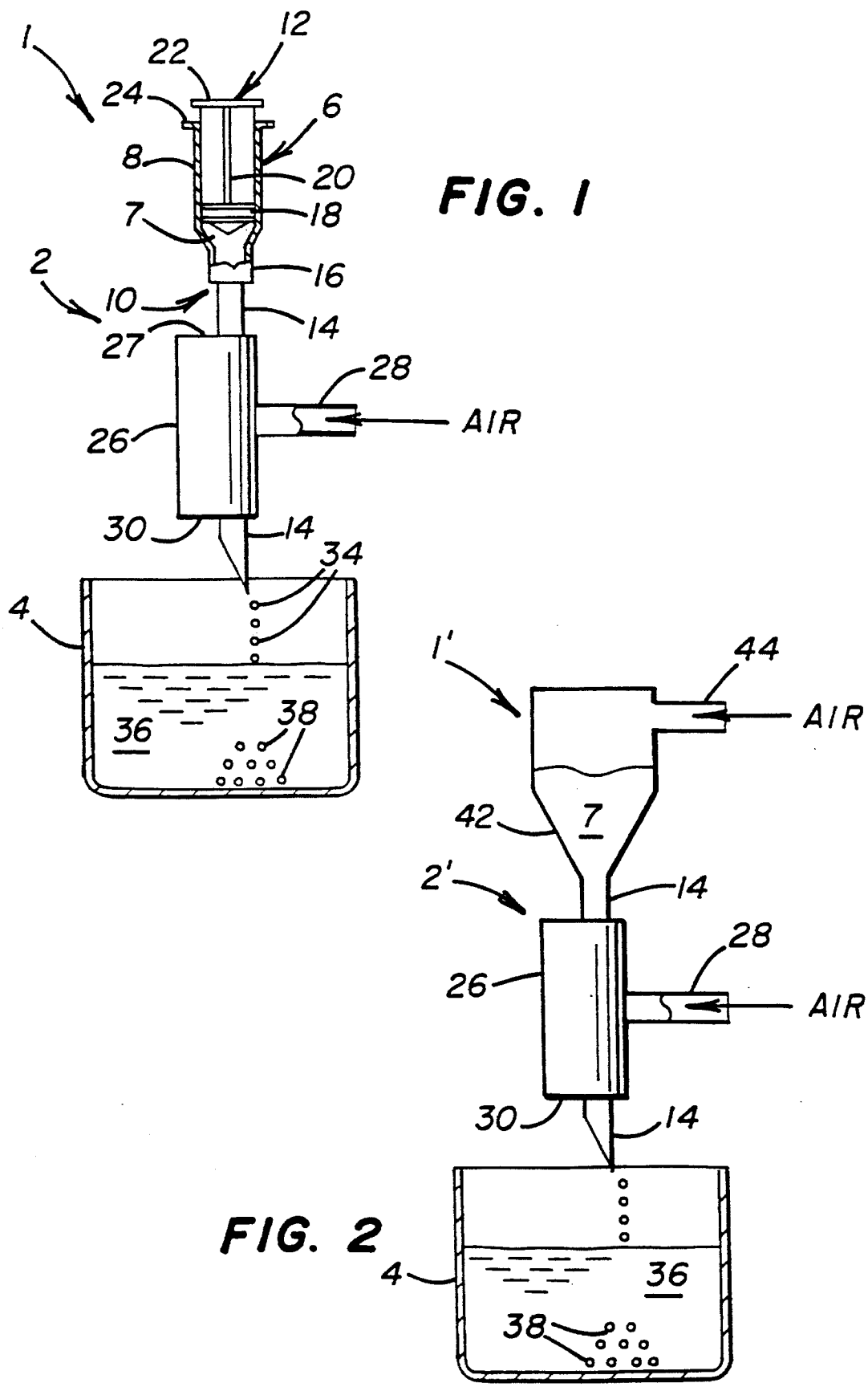

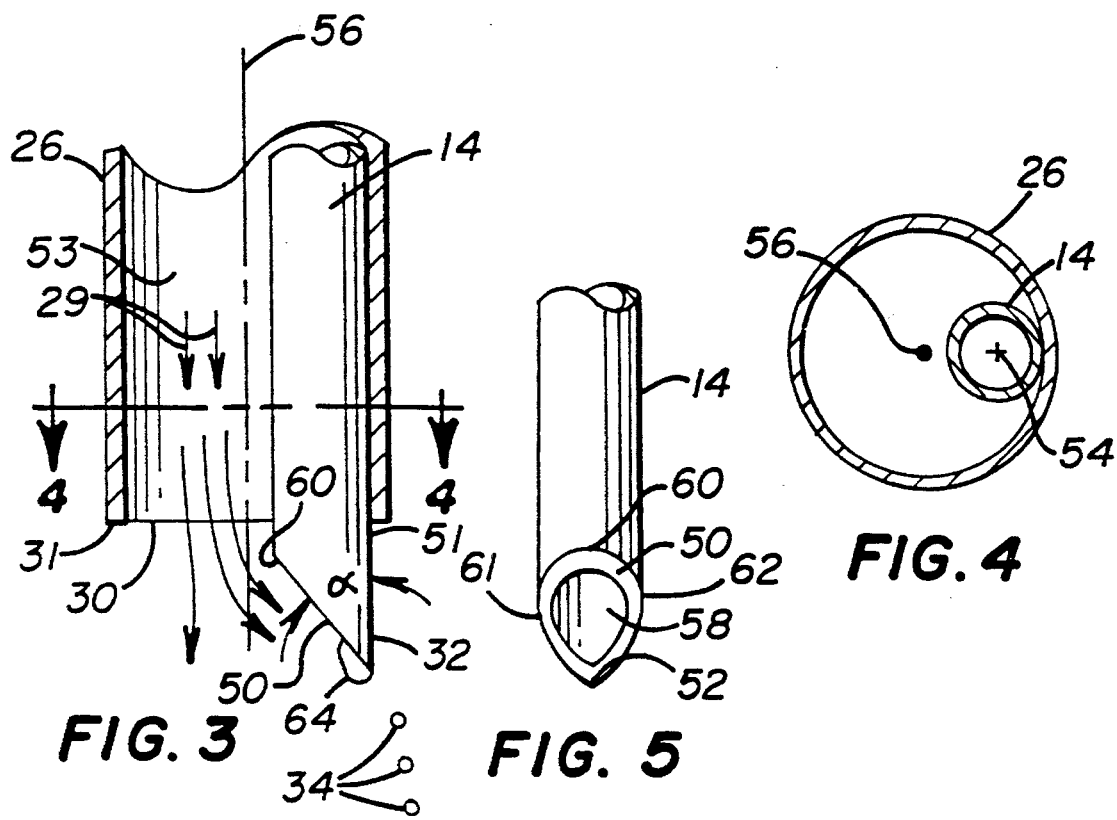
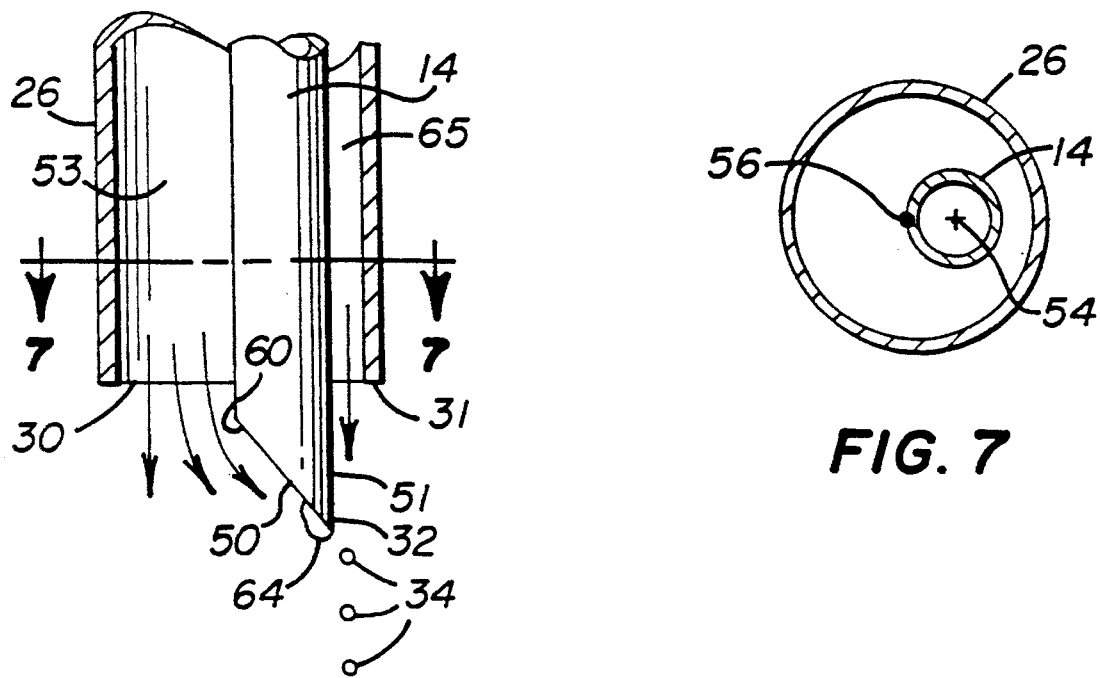

MICROCAPSULE GENERATING SYSTEM CONTAINING AN AIR KNIFE AND METHOD OF ENCAPSULATING

This application is related to copending application entitled "Multiple Layer Alginate Coatings of Biological Tissue for Transplantation", Ser. No. 08/186,327, filed on Jan. 24, 1994.

BACKGROUND OF THE INVENTION

1. Field of the Invention

The present invention concerns a microcapsule generating system and relates to encapsulation of material generally, and more particularly to encapsulating tissue or a suspension of cells so that the encapsulated tissue or cells remain viable within a protective membrane or coating. The membrane or coating is permeable to nutrients, ions, oxygen, and other materials needed both to maintain the tissue and to support its normal metabolic functions, but is impermeable to bacteria, lymphocytes, and large proteins of the type responsible for immunological reactions resulting in rejection.

Insulin-producing or other hormone-producing systems, cells from tissues, primary cultured cells, cultured cell lines that produce biological products of interest (such as Factor VIII and calcitonin), and genetically engineered cultured cell lines, for example, can be coated using the encapsulating apparatus of the present invention. That is, this apparatus permits encapsulation of mammalian pancreatic beta cells, alpha cells, intact islets of Langerhans, and other tissues or tissue fractions which secrete hormones. The encapsulated cells or tissue may be suspended in a culture medium where they will secrete hormones over an extended period.

2. Background Art and Related Art Disclosures

Various attempts have been made to provide semipermeable microcapsules that were both biocompatible with the body tissue and impermeable to the components of the immune system. Typically, living tissue or individual cells are suspended in an aqueous solution of a reversibly gelable material, such as sodium alginate, and droplets of this suspension are formed and allowed to fall into a gelling solution, such as calcium chloride. The temporary capsules so formed are then treated with a crosslinking polymer, such as polylysine and polyethyleneimine, to form an outer semipermeable coating.

The droplets are typically formed by feeding the alginate suspension to a first site where a mass of the liquid suspension accumulates. Then the mass of liquid suspension is agitated such that it is broken up into small droplets. Devices using vibration, centrifugal force, air currents and electrostatic charges have been used to agitate the liquid to generate the small droplets.

One drawback of conventional devices using vibration, centrifugal force and air currents is that the diameters of the microcapsules produced thereby are dependent on the sizes of the orifices through which the suspension is extruded and are typically 500 µm or greater with devices used for pancreatic islet encapsulation, where a relatively large bore diameter is dictated by the large size of islets (50–300 µm). Since oxygen diffusion is insufficient to maintain cell viability at distances exceeding about 150 µm, the cells in the center region of these microcapsules are routinely lost due to oxygen deprivation.

Although devices using electrostatic charges are claimed to produce microcapsules having diameters as small as 150 µm (see, e.g., U.S. Pat. No. 4,789,550 to Hommel, et al.), the blank microcapsules and microcapsules containing cells or tissue produced by electrostatic devices generally are the same size. Accordingly, the separation and differentiation between the blanks and the other microcapsules is difficult at best. In addition, in order to produce microcapsules of small diameter using this approach, it is necessary to use small bore needles which cannot accommodate the larger particles in the suspension and which tend to clog with high density cell or other particulate suspensions.

SUMMARY

The present invention is directed to a microcapsule formation device that significantly minimizes the problems and disadvantages presented in conventional devices. The invention accomplishes this goal by providing a microencapsulation system with a droplet-forming air knife that includes a capillary tube or needle and an air sleeve. The capillary tube or needle is adapted for coupling to a first source of fluid, such as an alginate suspension, from which droplets are to be formed. The air sleeve is adapted for coupling to a second source of fluid, for example, sterilized air. The discharge end of the capillary tube or needle is positioned in the immediate vicinity of the discharge end of the air sleeve so that air currents from the air sleeve increase the force acting on a nascent droplet of the first fluid at the discharge end of the capillary tube or needle and help break the droplet away from the needle to free fall into a gelling solution. That is, as the liquid suspension of the materials to be coated or encapsulated is discharged from the capillary tube or needle, pressurized air introduced into the air sleeve breaks the liquid suspension into tiny droplets.

According to a first embodiment of the invention, the center of the outlet opening of the needle is offset from the center axis of the air sleeve. Thus, the needle can be eccentrically positioned within the air sleeve of the needle with its outlet opening eccentrically positioned relative to the center axis of the sleeve, for example. It has been found that the eccentricity of the needle outlet and air sleeve enhances the ability of the device to produce very small droplets. In addition, it has been empirically determined that the greater eccentricity of the capillary tube or needle (or its outlet), the smaller the droplet size.

According to a second embodiment of the invention, the capillary tube has a beveled, pointed discharge end. This configuration also has been empirically shown to be important to the generation of very small droplets.

According to a further advantageous feature of the present invention, the entire beveled portion of the needle is positioned beyond the end of the air sleeve. It has been empirically determined that the optimal needle position for producing the smallest possible droplets is when the uppermost region of the beveled portion of the needle is spaced a very short predetermined distance (e.g., 1 mm) from the air sleeve outlet.

The air knife of the present invention described above can form very small alginate droplets containing suspension of individual cells or tissue. The droplets are sufficiently small so that upon contact with a gelling solution, such as $CaCl_2$, microcapsules are formed having diameters from about 20–300 µm, depending on the size of the tissue or cells being encapsulated. This is especially advantageous when the microcapsules are to be introduced into a patient. That is, the volume of material being introduced into the patient can be reduced since the membrane is close fit about the encapsulated biological material. The small size of the microcapsules also makes delivery to the patient less intrusive as smaller needles are required for injection into the patient. Since the microcapsules are less than about 300 μm in diameter, diffusion of oxygen to the center of the capsules is no longer a problem. It also has been found that blanks (microcapsules without cells or tissues), which are formed in the present encapsulation process, are about ten to fiftyfold smaller than the microcapsules containing cells or tissue and, thus, are readily distinguishable and separable from the encapsulated cells and/or tissue.

Another especially advantageous aspect of the device of the present invention is that it can be used to form a thin second coating on encapsulated cells or tissue while maintaining the diameter of the double or multiple-coated microcapsule within 10–40 μm of the diameter of the single-coated microcapsule. The second coating is formed by passing a suspension of the encapsulated cells or tissue in alginate solution through the needle while introducing pressurized air into the sleeve. The additional coating(s) ensure(s) that the cells or tissue are completely encapsulated.

A method of forming droplets according the invention is also disclosed. The method includes providing first and second tubes each having an outlet opening, positioning the outlet openings with respect to one another such that the second tube outlet opening is located in the flow path of the gas discharged from the tube outlet opening, the center of the second tube outlet opening being offset from the center axis of the first tube outlet opening causing pressurized gas to flow from the first tube outlet opening, and causing a fluid to flow from and be suspended from the end of the second tube outlet opening so that the gas flowing from said first tube outlet opening impinges fluid suspended from the second tube outlet opening to form droplets therefrom.

The above is a brief description of some deficiencies in the prior art and advantages of the present invention. Other features, advantages and embodiments of the invention will be apparent to those skilled in the art from the following description, accompanying drawings and appended claims.

BRIEF DESCRIPTION OF THE DRAWINGS

FIG. 1 is a diagrammatic elevational view of a microcapsule generating system in accordance with the principles of the present invention;

FIG. 2 is a diagrammatic elevational view of a further embodiment of the microcapsule generating system of FIG. 1;

FIG. 3 is an enlarged sectional view of the distal ends of the air knife discharge tubes used in the microcapsule generating systems of FIGS. 1 and 2, showing the inner tube or needle arranged such that it abuts against the inner surface of the outer tube or sleeve;

FIG. 4 is a sectional view taken along line 4—4 in FIG. 3;

FIG. 5 is a side elevational view of the inner tube of FIG. 3 shown rotated 90 degrees;

FIG. 6 is an enlarged sectional view of the distal ends of the air knife discharge tubes of FIGS. 1 and 2 showing the inner tube or needle arranged such that it is radially spaced from the inner surface of the outer tube of sleeve;

FIG. 7 is a sectional view taken along line 7—7 in FIG. 6;

DESCRIPTION OF THE PREFERRED EMBODIMENT

Figure 8:
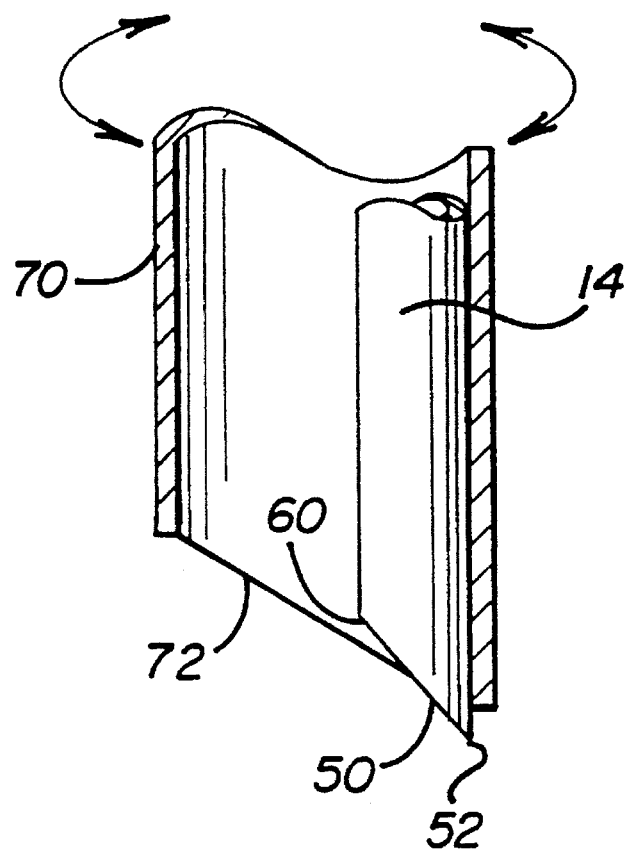
FIG. 8 is an enlarged sectional view of the distal ends of the air knife discharge tubes of FIGS. 1 and 2, showing the outer tube beveled according to another embodiment of the invention.
Figure 9:
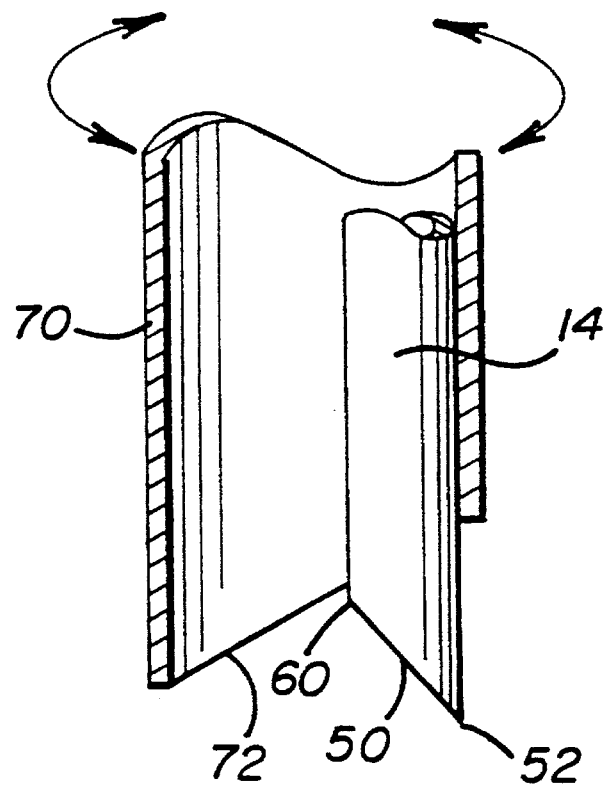
FIG. 9 is a further view of the beveled sleeve and needle of FIG. 8 with the outer tube shown rotated 90 degrees.

Referring to the drawings in detail wherein like numerals indicate like elements, a microencapsulation system is shown in FIG. 1 according to the principles of the present invention. Although the present invention can be used to encapsulate other materials, it will be described in conjunction with the encapsulation of droplets of an alginate suspension containing individual cells or tissue for purposes of simplification.

Referring to FIG. 1, microencapsulation system 1 generally comprises an air knife 2, which forms droplets 34 containing individual cells or tissue suspended in a gelable polymer solution, and a collection vessel or tank 4, which contains a gelling solution 36. Gelling solution 36 is positioned below the air knife for collecting the droplets 34 and causing microcapsules 38 containing the desired biological material to be formed.

Air knife 2 includes a syringe 6 for dispensing the material to be encapsulated, such as an alginate solution 7, and a tubular air sleeve 26 which will be described in more detail below. The syringe 6 includes a barrel 8, which is shown as containing the alginate suspension 7, a needle assembly 10, and a plunger 12 for forcing the alginate suspension through the needle assembly. Needle assembly 10 includes a capillary tube or needle 14 and hub 16 which fluidly couples needle 14 to barrel 8, so that fluid, such as alginate solution 7 can be dispensed from barrel 8 through needle 14.

Plunger 12 includes a piston 18 and a stem 20 which are interconnected so that piston 18 can be readily moved to displace alginate suspension 7 from barrel 8 into and through needle 14. A grip 22 and a finger ledge 24 also are provided as is conventionally known in the field, to facilitate the manual displacement of plunger 12. Preferably, a mechanical drive (not shown) can be coupled to the plunger to displace the plunger at a constant rate as would be apparent to one of ordinary skill.

Referring to FIGS. 1 and 3–5, tubular air sleeve 26 is positioned around part of the axial length of needle 14, i.e., needle 14 extends through sleeve 26. Sleeve 26 includes an end wall 27 through which needle 14 extends. End wall 27 and needle 14 form a closed end for sleeve 26 which includes an open distal end 30. A feed pipe 28 is fluidly coupled to air sleeve 26 for introducing pressurized gas, preferably sterilized air, into the flow path or space 53 formed between the outer wall surface of needle 14 and the inner wall surface of air sleeve 26. As will be described in more detail below, the pressurized air in air sleeve 26 controls, in part, the size of the droplets dispensed by needle 14. Air knife 2 is suspended above collection tank 4 with any suitable fixture as would be apparent to one of skill.

FIG. 2 illustrates a second embodiment of the microencapsulation system. System 1' differs from system 1 in that system 1' includes air knife 2' which does not include a plunger mechanism. In air knife 2', needle 14 is coupled to a container 42, which is configured to hold the fluid from which the droplets are to be made, such as alginate solution 7. Container 42 is coupled to a source of pressurized gas (preferably sterilized air) via a feed pipe 44. The pressure of the gas introduced into container 42 is controlled by conventional means to regulate the discharge rate of alginate suspension 7, for example, through needle 14. The discharge rate preferably is regulated to be constant.

Referring to FIGS. 3, 4 and 5, the configuration and position of tubular member or needle 14 relative to sleeve 26 will be discussed. In the preferred embodiment, needle 14 is positioned in sleeve 26, which has an elongated and hollow or tubular shape, and extends beyond outlet opening 30 of sleeve 26. Sleeve 26 can be made of stainless steel or any other suitable sterilizable material. Sleeve 26 terminates at its distal end into a generally blunt edge 31. That is, edge 31 is neither beveled nor sharp.

Needle 14 is an elongated tubular member that is hollow throughout its entire axial length. For the purpose of illustration, the size of needle 14 can range between 16 and 30 gauge, and preferably is 20 gauge. Distal end 32 of needle 14 is beveled at an angle α (the angle formed between side wall 51 of needle 14 and beveled surface 50). Angle α can range from about 15 degrees to 45 degrees to provide the desired results, and preferably is about 22°. As shown in FIG. 3, beveled surface 50 is positioned a short distance below blunt edge 31 of sleeve 26. Preferably the uppermost portion of beveled surface is about 1 mm below blunt edge 31. It should be understood, however, that the present invention contemplates positioning beveled surface 50 at various locations relative to blunt edge 31 of sleeve 26. In addition, although beveled surface 50 is shown facing the air flow path, variations to this position are also contemplated within the scope of the present invention.

Referring to FIG. 5, beveled (elliptical) surface 50 is bounded by an upper edge 60, and side edges 61 and 62 that meet at and terminate into a pointed tip 52. While beveled surface 50 is shown as being flat, it should be understood that beveled surface 50 could alternatively be arcuately shaped to provide an additional contact surface for the droplets to be formed thereon and, thus, help to control the droplet size. The beveled shape of edge 50 represents an important aspect of the present invention, in that the beveled edge allows air knife 2 (or 2') to generate smaller size droplets 34.

As illustrated in FIGS. 3 and 4, needle 14 preferably is eccentrically (i.e., non-coaxially) positioned inside sleeve 26. In other words, center 54 of needle outlet opening 58 is offset from center line (longitudinal central axis) 56 of sleeve 26. This eccentricity also is important to generate small diameter droplets 34. In the preferred embodiment, side wall 51 of needle 14 about the inner wall surface of sleeve 26, so as to prevent air from flowing therebetween.

The eccentric placement of needle 14 further contributes to the regulation of the size of the droplets formed and to the significant reduction of their size. Additionally, the beveled shape of needle 14 and the placement of needle 14 in contact with the inner wall surface of sleeve 26 cause the formation of blank microcapsules of much smaller size than the microcapsules containing cells or tissue. Consequently, the latter microcapsules are readily identifiable and distinguishable from the blank microcapsules, and thus segregable therefrom.

Referring now to FIGS. 6 and 7, there is illustrated an alternate embodiment of air knife 2. This embodiment is similar to the embodiment illustrated in FIGS. 3, 4 and 5, with the single variation that needle 14 is not placed in direct contact with the inner surface of sleeve 26. A spacing 65 is allowed to be formed between needle 14 and sleeve 26, through which pressurized air is allowed to flow.

The size of spacing 65, i.e., the distance between needle 14 and sleeve 26, varies with the desired application of microcapsule generating system 1. Generally, the farther needle 14 is from center axis 56 of sleeve 26 (i.e., the closer needle 14 is to the inner wall of sleeve 26), the fluid extruded through needle 14 tends to accumulate on the back side of beveled surface 50. In contrast to a configuration where the needle 14 is coaxially aligned with, or close to center axis 56 of sleeve 26, greater control to reduce the size of the capsules can be exercised due to increased air flow rate over tip 52 as the needle 14 is moved radially outward.

Turning now to FIGS. 8 and 9, there is illustrated another embodiment of air knife 2. The embodiment is similar to that shown in FIGS. 3, 4 and 5, except that air knife 2 includes a sleeve 70 that is similar in design and construction to sleeve 26, with the exception that sleeve 70 includes a beveled edge 72, rather than blunt edge 31.

The beveled edges 50 and 72 of needle 14 and sleeve 70, respectively, can be rotated relative to each other to attain the optimal desired droplet size and shape. FIG. 8 shows the two beveled edges 50 and 72 having their slopes in the same general direction, while FIG. 9 illustrates the slopes as being oppositely positioned.

The general operation of the device will be described in conjunction with the system illustrated in FIGS. 1 and 3–5 using a particulates suspension in an alginate solution for purposes of example and, thus, is not intended to limit the scope of the invention. Syringe 6 is provided with an alginate suspension and plunger 12 displaced at a constant rate (e.g., 0.1–2 ml/min depending on the size of needle 14 sleeve and the material to be encapsulated). As suspension 7 is discharged from outlet opening 58 in beveled surface 50 of needle 14, pressurized gas (e.g., air) as designated by arrow 29 concurrently is flowed downwardly through a chamber 53 formed between the inner surface of sleeve 26 and the outer surface of needle 14. Some of the gas exiting outlet opening 30 flows toward beveled surface 50 to agitate accumulation 64 of suspension 7 on surface 50. The air currents push the alginate suspension which accumulates at beveled surface 50 of needle 14, toward tip 52, thus forming droplets 34 having a desired shape and size. That is, the gas introduced through feed pipe 28 enters sleeve 26 and exits sleeve 26 via outlet opening 30 whereafter air currents agitate the alginate suspension accumulated on distal end 32 of needle or capillary tube 14 to form very small droplets 34. The droplets are captured in a gelling solution 36, such as calcium chloride solution. In the case where $CaCl_2$ is used, the calcium interacts with the carboxylic acid groups of the alginate to form calcium alginate gel. In general, droplets 34 have a substantially spherical shape. The air flow pressure and plunger speed are regulated so as to generate the desired droplet size and shape as discussed above.

Using the air knife of the present invention, biological material containing microcapsules having diameters from about 20–300 μm are formed. The blanks, microcapsules without biological material, are generally about ten to fiftyfold smaller. Thus, the microcapsules containing biological material are clearly distinguishable from the blank microcapsules based on size and are readily separated as described below.

The very small blank microcapsules are separated from the remaining microcapsules containing the coated biological material, by allowing the latter microcapsules, having a larger size, to settle out, and then by washing away the smaller blank microcapsules. The foregoing process of allowing the larger microcapsules to settle out in tank 4, and the washing away of the smaller blank microcapsules is repeated as many times as needed until the desired concentration of encapsulated islets or other tissue is attained.

Then, the collected encapsulated biological material may be over coated by repeating the process described above. Such over coating will ensure that tissue or cells are completely encapsulated.

The present invention will hereinafter be described more specifically by the following Examples which are provided for illustrative purposes and are not intended to limit the invention. In these examples, a system constructed according to microcapsule generation system 1 was used. The cell suspension in alginate solution was placed in the barrel of the syringe which includes a 20-gauge needle having a pointed tip beveled at a 22° angle. The uppermost edge 60 of beveled surface 50 was positioned about 1 mm below edge 30 of sleeve 26.

EXAMPLE 1

Encapsulation of Pancreatic Islets

A suspension of pancreatic islets in alginate is placed in the syringe barrel. The syringe plunger 12 is displaced to provide a flow rate of 0.3 ml/min to dispense the cell suspension in alginate solution from the needle while air is delivered to outer sleeve 26, which has a 2 mm inner diameter approximately, to provide an entry pressure in sleeve 26 of about 30 psi. Droplets of the suspension fall into collecting vessel 4 containing 120 mM $CaCl_2$ and 10 mM HEPES. The vessel is positioned so that the $CaCl_2$ is about 160–165 mm from tip 52 of the needle. The microcapsules containing pancreatic islets recovered with this procedure had a diameter of about 50 to 300 µm. On the other hand, the blank microcapsules obtained with this procedure had a diameter ranging between 1 µm and 20 µm. Consequently, the blank microcapsules containing islets are readily identifiable and distinguishable from the blank microcapsules for subsequent separation.

EXAMPLE 2

Encapsulation of Hepatocytes

Figure 10:
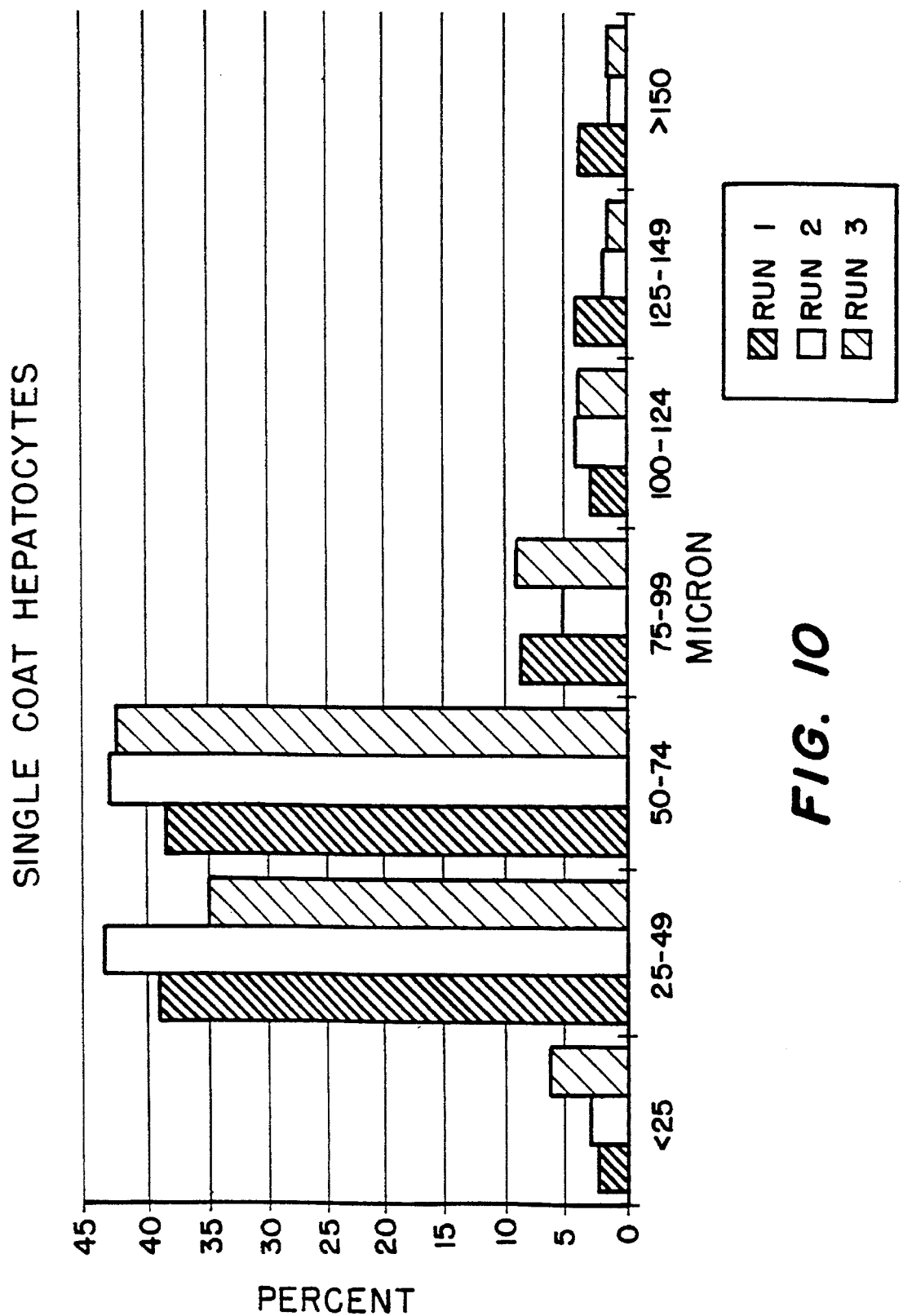
FIG. 10 is a graph illustrating the size distribution of single-coated microcapsules formed from three different preparations of hepatocytes under the same procedures using the system illustrated in FIGS. 1 and 3–5 (90% of the microcapsules have a diameter less than 75 μm)

An cell suspension in alginate solution comprising rat hepatocytes is prepared. The syringe plunger 12 is displaced to provide a flow rate of 0.3 ml/min. to dispense the suspension from the needle while air is delivered to outer sleeve 26, which has a 2 mm inner diameter approximately, to maintain an internal sheath entry pressure of about 30–33 psi. Droplets of the suspension fall into collecting vessel 4 containing 120 mM $CaCl_2$ and 10 mM HEPES. The vessel is positioned so that the $CaCl_2$ solution is about 160 mm from tip 52 of the needle. Over 90% of the microcapsules recovered with this procedure had a diameter of less than 75 µm. The size distribution is illustrated in FIG. 10 which shows three different preparations of hepatocytes which were run separately according to the procedures described in this example. The consistency of the data from each preparation indicates that these results are reproducible as required for commercial manufacturing.

EXAMPLE 3

Encapsulation of Proliferating Cells that Secrete Factor VIII

Figure 11:
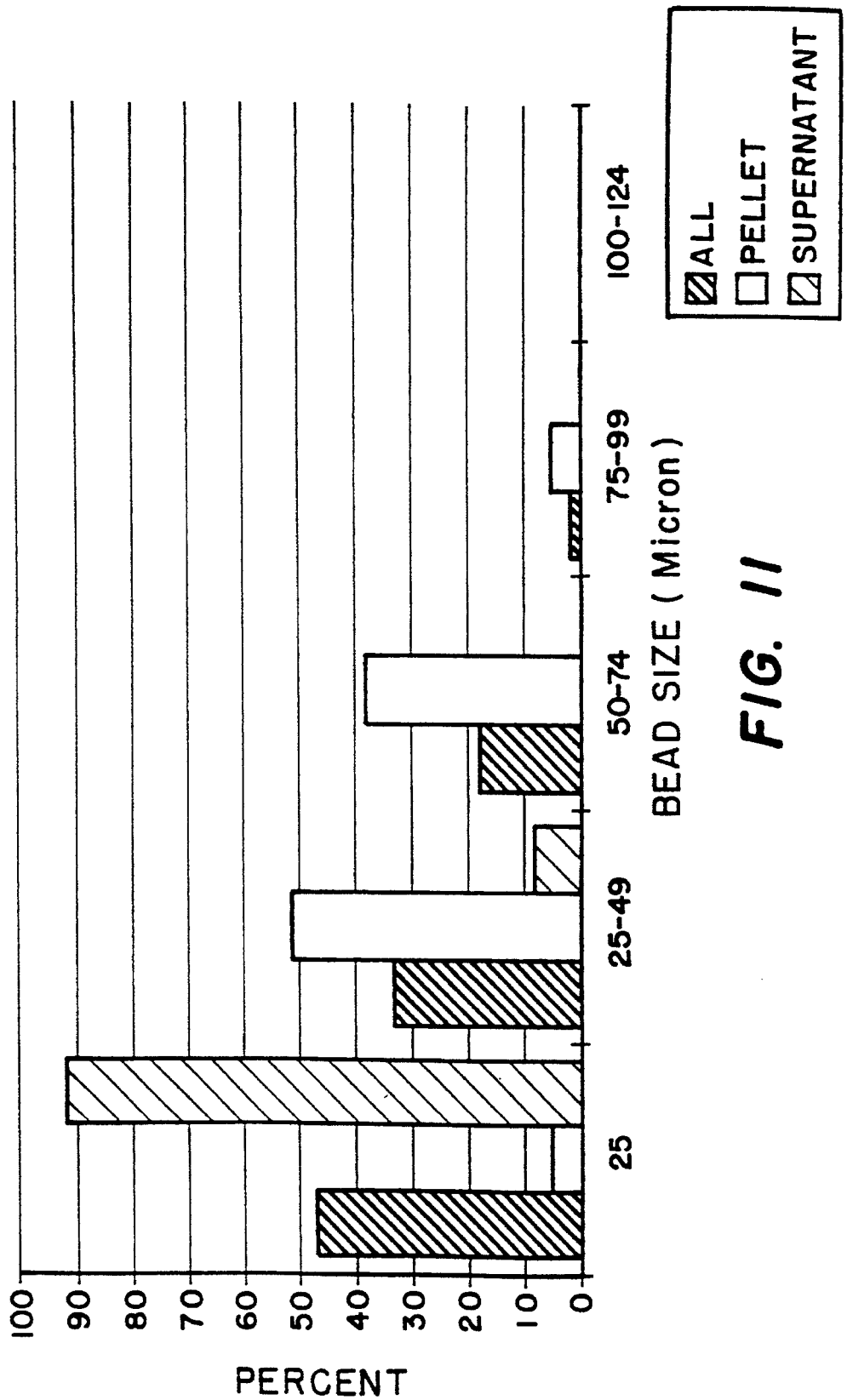
FIG. 11 is a graph illustrating the size distribution of single-coated microcapsules containing a proliferating cell line that provides Factor VIII using the system illustrated in FIGS. 1 and 3–5.

An alginate suspension comprising Factor VIII secreting cells is prepared. The syringe plunger 12 is displaced to provide a flow rate of 0.3 ml/min to dispense the alginate suspension from the needle while air is delivered to outer sleeve 26, which has a 2 mm inner diameter approximately, to provide a pressure of about 33 psi entering sleeve 26. Droplets of the alginate suspension fall into collecting vessel 4 containing 120 mM $CaCl_2$ and 10 mM HEPES. The vessel is positioned so that the $CaCl_2$ solution is about 154 mm from tip 52 of the needle. 90% of the microcapsules recovered with this procedure had a diameter between 25 and 75 µm. This size distribution is illustrated in FIG. 11 wherein (1) all, (2) pellet, and (3) supernatant correspond to (1) microcapsules containing cells together with blanks, (2) primarily microcapsules containing cells and (3) primarily blanks, respectively.

EXAMPLE 4

Encapsulation of Proliferating Cells that Secrete Calcitonin

Figure 12:
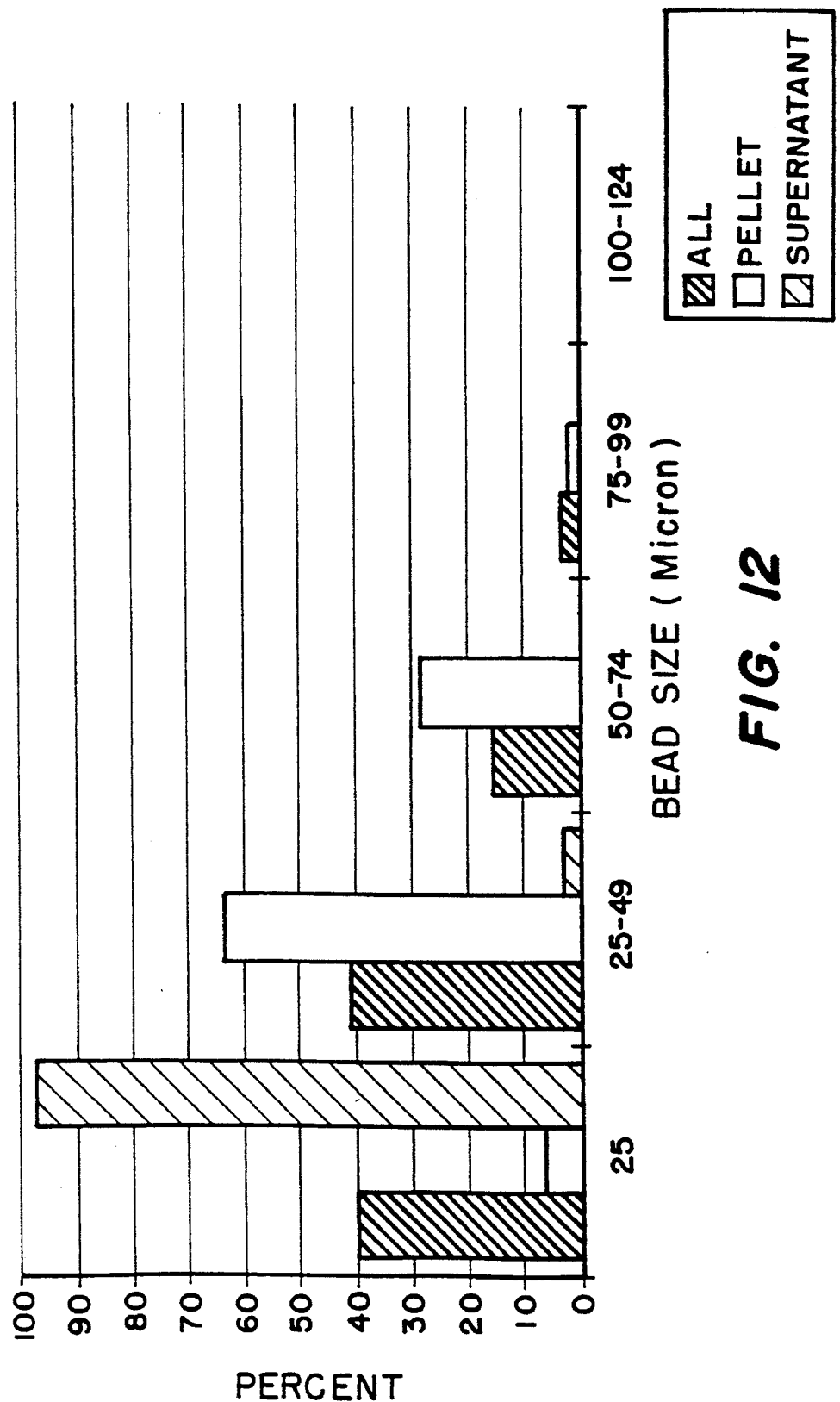
FIG. 12 is a graph illustrating the size distribution of single-coated microcapsules containing a proliferating cell line that secretes calcitonin.

An suspension of cells secreting calcitonin is prepared in alginate solution. The syringe plunger 12 is displaced at a travel speed of 0.3 ml/min to dispense the suspension from the needle while air is delivered to outer sleeve 26, which has a 2 mm inner diameter approximately, to maintain an internal pressure of about 33 psi entering sleeve 26. Droplets of the suspension fall into collecting vessel 4 containing 120 mM $CaCl_2$ and 10 mM HEPES. The vessel is positioned so that the $CaCl_2$ solution is about 154 mm from tip 52 of the needle. 90% of the microcapsules recovered with this procedure had a diameter between 25 and 75 µm. This size distribution is illustrated in FIG. 12 in which all, pelleted and supernatant have the same meanings as described in conjunction with Example 3 and FIG. 11.

The above is a detailed description of particular embodiments of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specifications should not be construed to unduly narrow the full scope of protection to which the invention is entitled.

What is claimed is:

1. A microcapsule generating system for forming droplets containing material to be encapsulated, including an air knife, comprising in combination:
   a. a container for retaining the material to be encapsulated and encapsulating material;
   b. a tubular needle having a proximal end connected to said container and an open distal end having a beveled end surface opposite to said proximal end through which said material to be encapsulated is discharged after passing through said needle from said container;

c. a tubular sleeve having an inner wall surrounding said needle and coupled to a source of gaseous fluid, said tubular sleeve having a longitudinal central axis, said sleeve being configured to route gaseous fluid flow from said source of gaseous fluid through an end opening of said sleeve such that said gas flow from said sleeve end opening is in a flow path essentially parallel to said central axis;

d. wherein said needle is disposed essentially adjacent said sleeve inner wall essentially parallel to the longitudinal central axis of said sleeve such that said distal end of said needle is disposed within said flow path of said gas and is at a position not centered within said sleeve end opening; and e. wherein said distal end of said needle is beveled at an angle with the inner wall of said sleeve of about 15 degrees to about 45 degree and the beveled end is disposed facing the central axis of said sleeve and to extend a distance at least partially beyond said tube opening.

2. A microcapsule generating system according to claim 1, wherein the beveled surface of said distal end is essentially elliptically shaped, and is defined by an upper edge which connect with two side edges that continue around the perimeter of said open distal end to meet and terminate at a pointed tip.

3. A microcapsule generating system according to claim 1, wherein said distance is about 1 millimeter.

4. A microcapsule generating system according to claim 3, wherein said beveled surface is essentially flat.

5. A microcapsule generating system according to claim 3, further including a collection tank containing a hardening solution positioned to collect droplets of the material to be encapsulated formed after the material to be encapsulated is discharged from the open distal end of said needle, said hardening solution causing microcapsules to form from the droplets containing the material to be encapsulated.

6. A microcapsule generating system according to claim 1, wherein a perimeter of said sleeve end opening at said end of said sleeve terminates in a surface which is beveled with respect to said central axis.

7. A microcapsule generating system according to claim 1, wherein the beveled surface of said distal end is a essentially continuous surface across the full width of the perimeter of the tube of said needle resulting in a needle point at one location on a perimeter edge of the tube of the needle.

8. A method of forming droplets with the system of claim 1 comprising:

causing pressurized gaseous fluid to force the material to be encapsulated and the encapsulating material out of the container into the needle to form fluid suspended form the needle end opening, and causing a gaseous fluid to flow through the sleeve and out of the sleeve end opening to impinge the fluid suspended from the needle end opening to form said droplets.

9. The method according to claim 8 wherein the material encapsulated is biological material.

10. The method according to claim 8 wherein blank droplets not containing biological material are also formed.

11. The method according to claim 9 wherein the biological material is cells.

* * * * *

UNITED STATES PATENT AND TRADEMARK OFFICE
CERTIFICATE OF CORRECTION

PATENT NO. : 5,521,079
DATED : MAY 28, 1996
INVENTOR(S) : RANDEL E. DORIAN, et. al.

It is certified that error appears in the above-identified patent and that said Letters Patent is hereby corrected as shown below:

On the title page: Item [73]
    Assignee: Add -- Metabolex, Inc., Hayward, California--;

Signed and Sealed this

First Day of April, 1997

Attest:

BRUCE LEHMAN

Attesting Officer

Commissioner of Patents and Trademarks